(12) United States Patent
Kwok et al.

(10) Patent No.: US 8,122,886 B2
(45) Date of Patent: *Feb. 28, 2012

(54) RESPIRATORY MASK ASSEMBLY WITH VENT

(75) Inventors: Philip Rodney Kwok, Chatswood (AU); Perry David Lithgow, Glenwood (AU)

(73) Assignee: ResMed Limited, Bella Vista (AU)

( * ) Notice: Subject to any disclaimer, the term of this patent is extended or adjusted under 35 U.S.C. 154(b) by 1138 days.

This patent is subject to a terminal disclaimer.

(21) Appl. No.: 11/645,582

(22) Filed: Dec. 27, 2006

(65) Prior Publication Data

US 2007/0101998 A1    May 10, 2007

Related U.S. Application Data

(63) Continuation of application No. 10/364,358, filed on Feb. 12, 2003, now Pat. No. 7,207,335, which is a continuation of application No. 09/021,541, filed on Feb. 10, 1998, now Pat. No. 6,561,190.

(30) Foreign Application Priority Data

Feb. 10, 1997  (AU) ........................ PO5045

(51) Int. Cl.
*A62B 18/02* (2006.01)
*A62B 18/00* (2006.01)
(52) U.S. Cl. .......... 128/206.21; 128/205.25; 128/200.24
(58) Field of Classification Search .................. 128/857, 128/858, 863, 200.24, 201.22–201.29, 204.18, 128/204.23, 204.25, 205.24, 206.21–207.13; 604/126, 254, 247; 24/713.6, 662
See application file for complete search history.

(56) References Cited

U.S. PATENT DOCUMENTS

| 781,516 A | 1/1905 | Guthrie |
|---|---|---|
| 812,706 A | 2/1906 | Warbasse |
| 835,075 A | 11/1906 | Mahaffy |
| 1,081,145 A | 12/1913 | Johnston et al. |
| 1,192,186 A | 7/1916 | Greene |
| 1,653,572 A | 12/1927 | Jackson |
| 1,926,027 A | 9/1933 | Biggs |
| 2,008,677 A | 7/1935 | Booharin |
| 2,102,037 A | 12/1937 | Schwartz |
| 2,123,353 A | 7/1938 | Catt |
| 2,248,477 A | 7/1941 | Lombard |

(Continued)

FOREIGN PATENT DOCUMENTS

AU          91/77110 B       11/1991

(Continued)

OTHER PUBLICATIONS

Office Action in Japanese Appln. No. 2004-197875 (Oct. 9, 2007) with English translation.

(Continued)

*Primary Examiner* — Annette Dixon
(74) *Attorney, Agent, or Firm* — Nixon & Vanderhye, PC

(57) ABSTRACT

A mask (10) for use with a system for supplying breathable gas pressurized above atmospheric pressure to a human or animal's airways. The mask (10) includes a mask shell (12) which is, in use, in fluid communication with a gas supply conduit (30), and a gas washout vent assembly (20). At least the region of the mask shell (12) or conduit (30) surrounding or adjacent the vent assembly is formed from a relatively flexible elastomeric material.

106 Claims, 6 Drawing Sheets

U.S. PATENT DOCUMENTS

| | | |
|---|---|---|
| 2,254,854 A | 9/1941 | O'Connell |
| 2,259,817 A | 10/1941 | Hawkins |
| 2,317,608 A | 4/1943 | Heldbrink |
| 2,311,608 A | 9/1943 | Heidbrink |
| 2,371,965 A | 3/1945 | Lehmberg |
| 2,376,871 A | 5/1945 | Fink |
| 2,415,846 A | 2/1947 | Randall |
| 2,438,058 A | 3/1948 | Kincheloe |
| 2,578,621 A | 12/1951 | Yant |
| 2,843,121 A | 7/1958 | Hudson |
| 2,872,923 A | 2/1959 | Birch et al. |
| 2,931,366 A | 4/1960 | Schwarz |
| D188,084 S | 5/1960 | Garelick |
| 2,939,458 A | 6/1960 | Lundquist |
| 3,013,556 A | 12/1961 | Galleher |
| 3,162,411 A | 12/1964 | Duggan |
| 3,182,659 A * | 5/1965 | Blount ..................... 128/207.12 |
| 3,189,027 A | 6/1965 | Bartlett |
| 3,238,943 A | 3/1966 | Holley |
| 3,291,127 A | 12/1966 | Eimer et al. |
| 3,315,674 A | 4/1967 | Bloom et al. |
| 3,330,273 A | 7/1967 | Bennett |
| 3,362,420 A | 1/1968 | Blackburn et al. |
| 3,363,833 A | 1/1968 | Laerdal |
| 3,412,231 A | 11/1968 | McElligott |
| 3,490,452 A * | 1/1970 | Greenfield ............... 128/200.23 |
| 3,513,844 A | 5/1970 | Smith |
| 3,556,122 A | 1/1971 | Laerdal |
| 3,580,051 A | 5/1971 | Blevins |
| 3,680,556 A | 8/1972 | Morgan |
| 3,700,000 A | 10/1972 | Hesse et al. |
| 3,720,235 A | 3/1973 | Schrock |
| 3,762,747 A * | 10/1973 | Griffen ......................... 403/225 |
| 3,796,216 A | 3/1974 | Schwarz |
| 3,799,164 A | 3/1974 | Rollins |
| D231,803 S | 6/1974 | Huddy |
| 3,850,171 A | 11/1974 | Ball et al. |
| 3,866,095 A | 2/1975 | Marmorek |
| 3,868,164 A | 2/1975 | Lisk |
| 3,877,425 A | 4/1975 | O'Neill |
| 3,942,403 A | 3/1976 | Pramberger |
| 3,949,743 A * | 4/1976 | Shanbrom ................ 128/200.14 |
| 3,958,275 A | 5/1976 | Morgan et al. |
| 4,037,142 A | 7/1977 | Poole |
| 4,077,404 A | 3/1978 | Elam |
| D250,131 S | 10/1978 | Lewis et al. |
| 4,137,602 A * | 2/1979 | Klumpp, Jr. ..................... 16/2.1 |
| 4,167,185 A | 9/1979 | Lewis |
| 4,201,205 A * | 5/1980 | Bartholomew .......... 128/205.25 |
| 4,219,020 A | 8/1980 | Czajka |
| 4,226,234 A | 10/1980 | Gunderson |
| 4,245,632 A | 1/1981 | Houston |
| 4,258,710 A | 3/1981 | Reber |
| 4,266,540 A | 5/1981 | Panzik et al. |
| 4,274,406 A | 6/1981 | Bartholomew |
| 4,276,877 A | 7/1981 | Gdulla |
| D262,322 S | 12/1981 | Mizerak |
| 4,304,229 A | 12/1981 | Curtin |
| 4,328,797 A | 5/1982 | Rollins, III et al. |
| 4,347,205 A | 8/1982 | Stewart |
| 4,354,488 A * | 10/1982 | Bartos ...................... 128/205.25 |
| 4,363,580 A * | 12/1982 | Bell ................................ 411/15 |
| 4,402,316 A | 9/1983 | Gadberry |
| 4,408,818 A | 10/1983 | Markarian |
| 4,412,537 A | 11/1983 | Tiger |
| 4,440,163 A * | 4/1984 | Spergel .................... 128/205.13 |
| 4,454,881 A | 6/1984 | Huber et al. |
| 4,467,799 A | 8/1984 | Steinberg |
| 4,522,639 A | 6/1985 | Ansite et al. |
| 4,535,767 A | 8/1985 | Tiep et al. |
| 4,558,710 A | 12/1985 | Eichler |
| 4,559,939 A | 12/1985 | Levine et al. |
| 4,580,556 A | 4/1986 | Kondur |
| 4,616,647 A | 10/1986 | McCreadie |
| 4,622,964 A | 11/1986 | Flynn |
| 4,648,394 A | 3/1987 | Wise |
| 4,649,912 A | 3/1987 | Collins |
| 4,655,213 A | 4/1987 | Rapoport et al. |
| 4,665,570 A | 5/1987 | Davis |
| 4,671,271 A | 6/1987 | Bishop et al. |
| 4,677,975 A | 7/1987 | Edgar et al. |
| 4,677,977 A | 7/1987 | Wilcox |
| D293,613 S | 1/1988 | Wingler |
| 4,739,755 A | 4/1988 | White et al. |
| 4,770,169 A | 9/1988 | Schmoegner et al. |
| 4,774,941 A | 10/1988 | Cook |
| 4,774,946 A | 10/1988 | Ackerman |
| 4,782,832 A | 11/1988 | Trimble et al. |
| 4,799,477 A | 1/1989 | Lewis |
| 4,809,692 A | 3/1989 | Nowacki et al. |
| 4,819,629 A | 4/1989 | Jonson |
| 4,821,713 A | 4/1989 | Bauman |
| 4,841,953 A | 6/1989 | Dodrill |
| 4,848,334 A | 7/1989 | Bellm |
| 4,848,366 A | 7/1989 | Aita et al. |
| 4,907,584 A | 3/1990 | McGinnis |
| 4,910,806 A | 3/1990 | Baker et al. |
| 4,915,105 A | 4/1990 | Lee |
| 4,919,128 A | 4/1990 | Kopala et al. |
| 4,938,210 A | 7/1990 | Shene |
| 4,938,212 A | 7/1990 | Gnook et al. |
| 4,944,310 A | 7/1990 | Sullivan |
| D310,431 S | 9/1990 | Bellm |
| 4,969,901 A * | 11/1990 | Binder ........................ 623/17.18 |
| 4,971,051 A | 11/1990 | Toffolon |
| 4,974,586 A | 12/1990 | Wandel et al. |
| 4,986,269 A | 1/1991 | Hakkinen |
| 4,989,596 A | 2/1991 | Macris et al. |
| 4,989,599 A | 2/1991 | Carter |
| 5,005,568 A | 4/1991 | Loescher et al. |
| 5,005,571 A | 4/1991 | Dietz |
| 5,018,519 A | 5/1991 | Brown |
| 5,038,776 A | 8/1991 | Harrison et al. |
| 5,042,473 A | 8/1991 | Lewis |
| 5,042,478 A | 8/1991 | Kopala et al. |
| 5,046,200 A | 9/1991 | Feder |
| 5,046,512 A | 9/1991 | Murchie |
| 5,063,922 A | 11/1991 | Hakkinen |
| 5,065,756 A | 11/1991 | Rapoport |
| D322,318 S | 12/1991 | Sullivan |
| 5,069,205 A | 12/1991 | Urso |
| 5,069,222 A | 12/1991 | McDonald, Jr. |
| 5,069,586 A * | 12/1991 | Casey .......................... 411/339 |
| 5,080,094 A | 1/1992 | Tayebi |
| D323,908 S | 2/1992 | Hollister et al. |
| 5,109,839 A | 5/1992 | Blasdell et al. |
| 5,109,840 A | 5/1992 | Daleiden |
| 5,117,819 A * | 6/1992 | Servidio et al. .......... 128/204.18 |
| 5,121,745 A | 6/1992 | Israel |
| 5,133,347 A | 7/1992 | Huennebeck |
| 5,140,982 A | 8/1992 | Bauman |
| 5,148,802 A | 9/1992 | Sanders et al. |
| 5,159,938 A | 11/1992 | Laughlin |
| 5,178,138 A | 1/1993 | Walstrom et al. |
| D334,633 S | 4/1993 | Rudolph |
| 5,231,983 A | 8/1993 | Matson et al. |
| 5,233,978 A | 8/1993 | Callaway |
| 5,243,971 A * | 9/1993 | Sullivan et al. .......... 128/205.25 |
| 5,265,595 A | 11/1993 | Rudolph |
| 5,269,296 A | 12/1993 | Landis |
| 5,279,289 A | 1/1994 | Kirk |
| 5,280,784 A | 1/1994 | Kohler |
| 5,297,544 A | 3/1994 | May |
| 5,311,862 A | 5/1994 | Blasdell et al. |
| 5,322,057 A | 6/1994 | Raabe et al. |
| 5,343,878 A | 9/1994 | Scarberry et al. |
| 5,357,951 A | 10/1994 | Ratner |
| 5,358,340 A * | 10/1994 | Bober ........................... 384/125 |
| 5,368,020 A | 11/1994 | Beux |
| 5,372,130 A | 12/1994 | Stern et al. |
| 5,388,571 A | 2/1995 | Roberts et al. |
| 5,404,871 A | 4/1995 | Goodman et al. |
| 5,419,318 A | 5/1995 | Tayebi |
| 5,429,126 A | 7/1995 | Bracken |
| 5,429,683 A | 7/1995 | Le Mitouard |
| 5,431,158 A | 7/1995 | Tirotta |
| 5,438,981 A | 8/1995 | Starr et al. |

| | | | |
|---|---|---|---|
| 5,441,046 A | 8/1995 | Starr et al. | |
| D362,061 S | 9/1995 | McGinnis et al. | |
| 5,477,852 A | 12/1995 | Landis et al. | |
| 5,479,920 A | 1/1996 | Piper et al. | |
| 5,488,948 A | 2/1996 | Dubruille et al. | |
| 5,492,116 A | 2/1996 | Scarberry et al. | |
| 5,501,214 A | 3/1996 | Sabo | |
| 5,509,404 A | 4/1996 | Lloyd et al. | |
| 5,517,986 A | 5/1996 | Starr et al. | |
| 5,533,506 A | 7/1996 | Wood | |
| 5,538,000 A | 7/1996 | Rudolph | |
| 5,540,223 A | 7/1996 | Starr et al. | |
| 5,542,128 A | 8/1996 | Lomas | |
| RE35,339 E | 10/1996 | Rapoport | |
| 5,560,354 A | 10/1996 | Berthon-Jones et al. | |
| 5,570,682 A | 11/1996 | Johnson | |
| 5,570,689 A | 11/1996 | Starr et al. | |
| 5,575,277 A | 11/1996 | Lutz et al. | |
| D377,089 S | 12/1996 | Starr et al. | |
| 5,592,938 A | 1/1997 | Scarberry et al. | |
| 5,608,647 A | 3/1997 | Rubsamen et al. | |
| 5,642,730 A | 7/1997 | Baran | |
| 5,645,049 A | 7/1997 | Foley et al. | |
| 5,647,355 A | 7/1997 | Starr et al. | |
| 5,647,357 A | 7/1997 | Barnett et al. | |
| 5,649,532 A | 7/1997 | Griffiths | |
| 5,649,533 A | 7/1997 | Oren | |
| 5,655,520 A | 8/1997 | Howe et al. | |
| 5,655,527 A | 8/1997 | Scarberry et al. | |
| 5,657,493 A | 8/1997 | Ferrero et al. | |
| 5,657,752 A | 8/1997 | Landis et al. | |
| 5,660,566 A | 8/1997 | Ohsumi | |
| 5,662,101 A | 9/1997 | Ogden et al. | |
| 5,666,946 A | 9/1997 | Langenback | |
| 5,685,296 A | 11/1997 | Zdrojkowski et al. | |
| 5,687,715 A | 11/1997 | Landis et al. | |
| 5,715,741 A * | 2/1998 | Gasser et al. | 99/295 |
| 5,715,814 A | 2/1998 | Ebers | |
| 5,724,965 A | 3/1998 | Handke et al. | |
| 5,732,695 A | 3/1998 | Metzger | |
| 5,746,201 A | 5/1998 | Kidd | |
| 5,765,553 A | 6/1998 | Richards et al. | |
| 5,813,423 A | 9/1998 | Kirchgeorg | |
| 5,832,918 A | 11/1998 | Pantino | |
| 5,839,433 A * | 11/1998 | Higenbottam | 128/204.21 |
| 5,857,460 A * | 1/1999 | Popitz | 128/206.21 |
| 5,878,742 A * | 3/1999 | Figueredo et al. | 128/201.24 |
| 5,897,396 A | 4/1999 | Maejima | |
| 5,921,239 A | 7/1999 | McCall et al. | |
| 5,937,851 A | 8/1999 | Serowski et al. | |
| 6,006,748 A | 12/1999 | Hollis | |
| 6,012,455 A | 1/2000 | Goldstein | |
| 6,019,101 A | 2/2000 | Cotner et al. | |
| 6,039,044 A | 3/2000 | Sullivan | |
| 6,112,746 A | 9/2000 | Kwok et al. | |
| 6,119,693 A | 9/2000 | Kwok et al. | |
| 6,119,694 A | 9/2000 | Correa et al. | |
| 6,135,109 A | 10/2000 | Blasdell et al. | |
| 6,192,886 B1 | 2/2001 | Rudolph | |
| 6,309,438 B1 | 10/2001 | Kanno et al. | |
| 6,431,172 B1 | 8/2002 | Bordewick | |
| 6,435,181 B1 * | 8/2002 | Jones et al. | 128/204.18 |
| 6,478,026 B1 | 11/2002 | Wood | |
| 6,561,190 B1 * | 5/2003 | Kwok | 128/207.12 |
| 6,561,191 B1 * | 5/2003 | Kwok | 128/207.12 |
| 6,581,594 B1 | 6/2003 | Drew et al. | |
| 6,584,976 B2 | 7/2003 | Japuntich et al. | |
| 6,595,215 B2 | 7/2003 | Wood | |
| 6,644,316 B2 | 11/2003 | Bowman et al. | |
| 6,668,830 B1 * | 12/2003 | Hansen et al. | 128/206.21 |
| 6,792,623 B2 * | 9/2004 | Luppi | 2/171.3 |
| 6,823,865 B2 | 11/2004 | Drew et al. | |
| 7,159,587 B2 | 1/2007 | Drew et al. | |
| 7,207,335 B2 * | 4/2007 | Kwok et al. | 128/207.12 |
| 2002/0162558 A1 | 11/2002 | Noble | |
| 2003/0079751 A1 * | 5/2003 | Kwok | 128/206.15 |
| 2003/0116160 A1 | 6/2003 | Kwok et al. | |
| 2003/0172936 A1 | 9/2003 | Wilkie et al. | |
| 2004/0065327 A1 | 4/2004 | Gradon et al. | |
| 2004/0065330 A1 | 4/2004 | Landis | |
| 2004/0182397 A1 | 9/2004 | Wood | |
| 2004/0226566 A1 | 11/2004 | Gunaratnam et al. | |
| 2004/0261797 A1 | 12/2004 | White | |
| 2005/0011524 A1 | 1/2005 | Thomlinson | |
| 2005/0028821 A1 | 2/2005 | Wood et al. | |
| 2005/0028822 A1 | 2/2005 | Sleeper | |
| 2005/0005117 A1 | 3/2005 | Wood | |
| 2005/0076913 A1 | 4/2005 | Ho | |
| 2005/0092326 A1 | 5/2005 | Drew et al. | |
| 2005/0199242 A1 | 9/2005 | Matula | |
| 2006/0196509 A1 | 9/2006 | Drew et al. | |

FOREIGN PATENT DOCUMENTS

| | | |
|---|---|---|
| AU | 94/64816 B | 12/1994 |
| AU | 95/16178 B | 7/1995 |
| AU | 9459430 | 2/1996 |
| AU | A 32914/95 | 2/1996 |
| AU | A 41018/97 | 4/1998 |
| AU | A 89312/98 | 1/1999 |
| AU | 712236 | 4/1999 |
| CA | 1039144 | 9/1978 |
| DE | 459104 | 4/1928 |
| DE | 701 690 | 1/1941 |
| DE | 159396 | 6/1981 |
| DE | 3015279 A1 | 10/1981 |
| DE | 3345067 A1 | 6/1984 |
| DE | 3537507 A1 | 4/1987 |
| DE | 3539073 A1 | 5/1987 |
| DE | 4004157 C1 | 4/1991 |
| DE | 4343205 A1 | 6/1995 |
| DE | 197 35 359 | 1/1998 |
| DE | 297 23 101 | 7/1998 |
| DE | 298 10846 U1 | 8/1998 |
| EP | 0 054 154 | 10/1981 |
| EP | 0 252 052 A1 | 1/1988 |
| EP | 0 264 772 A1 | 4/1988 |
| EP | 0 386 605 A1 | 2/1990 |
| EP | 0427474 A2 | 5/1991 |
| EP | 0 462 701 A1 | 12/1991 |
| EP | 0 602 424 | 11/1993 |
| EP | 0601708 | 6/1994 |
| EP | 0 608 684 A1 | 8/1994 |
| EP | 0 658 356 | 6/1995 |
| EP | 0 697 225 | 7/1995 |
| EP | 0697 225 A2 | 7/1995 |
| EP | 0 697 225 A2 | 2/1996 |
| EP | 0 697 255 A | 2/1996 |
| EP | 178 925 A2 | 4/1996 |
| EP | 0 747 078 A2 | 12/1996 |
| EP | 0 821 978 | 2/1998 |
| EP | 1 027 905 A | 8/2000 |
| EP | 1 163 923 A2 | 6/2001 |
| FR | 2 574 657 A1 | 6/1986 |
| FR | 2 658 725 A1 | 8/1991 |
| FR | 2 749 176 | 12/1997 |
| GB | 1395391 | 5/1975 |
| GB | 1 467 828 | 3/1977 |
| GB | 2145335 A | 3/1985 |
| GB | 2147506 A | 5/1985 |
| GB | 2 164 569 A | 3/1986 |
| GB | 2 236 681 A | 4/1991 |
| GB | 2 267 648 A | 12/1993 |
| JP | 463702 | 5/1971 |
| JP | 463703 | 6/1971 |
| JP | 57-1477 | 11/1982 |
| JP | 63105772 | 5/1988 |
| JP | 2-141775 | 11/1990 |
| JP | 7000521 | 1/1995 |
| JP | 9010311 | 1/1997 |
| JP | 09/216240 A | 8/1997 |
| JP | A-11-267234 | 10/1999 |
| JP | A-2000-140587 | 5/2000 |
| JP | 2001-511035 | 8/2001 |
| JP | 2001-333982 | 12/2001 |
| JP | 2002-95751 | 4/2002 |
| JP | 2004-535226 | 11/2004 |
| WO | WO 80/01044 | 5/1980 |
| WO | WO 82/03548 | 10/1982 |

| | | |
|---|---|---|
| WO | WO 84/01293 | 4/1984 |
| WO | WO 86/06969 | 12/1986 |
| WO | WO 87/01950 | 4/1987 |
| WO | WO 91/03277 | 3/1991 |
| WO | WO 92/15353 | 9/1992 |
| WO | WO 92/20395 | 11/1992 |
| WO | WO 93/01854 | 2/1993 |
| WO | WO 94/02190 | 2/1994 |
| WO | WO 94/16759 | 8/1994 |
| WO | WO 94/20051 | 9/1994 |
| WO | WO 95/02428 | 1/1995 |
| WO | WO 96/25983 | 8/1996 |
| WO | WO 96/39206 | 12/1996 |
| WO | WO 97/07847 | 3/1997 |
| WO | WO 97/41911 | 11/1997 |
| WO | WO 98/04310 | 2/1998 |
| WO | WO 98/11930 | 3/1998 |
| WO | WO 98/18514 | 5/1998 |
| WO | WO 98/17643 | 6/1998 |
| WO | WO 98/24499 | 6/1998 |
| WO | WO 98/26829 | 6/1998 |
| WO | WO 98/26830 | 6/1998 |
| WO | WO 98/34665 | 8/1998 |
| WO | WO 98/48878 | 11/1998 |
| WO | WO 99/04842 | 2/1999 |
| WO | WO 00/13751 | 3/2000 |
| WO | WO 00/74758 | 12/2000 |
| WO | WO 01/26722 | 4/2001 |
| WO | WO 01/89381 | 11/2001 |
| WO | WO 01/97892 | 12/2001 |
| WO | WO 02/096342 | 12/2002 |
| WO | WO 2004/073778 | 9/2004 |
| WO | WO 2005/063328 | 7/2005 |
| WO | WO 2005/079726 | 9/2005 |

OTHER PUBLICATIONS

U.S. Appl. No. 10/298,845, Kwok, filed Nov. 2002.
Mask 1 Photographs; Respironics Inc., Reusable Full Mask (small) Part # 462033 Lot #951108.
Mask 2 Photographs, Puritan—Bennett, Adam Curcuit , Shell Part # 231700, Swivel Part # 616329-00, Pillows (medium) Part #616324.
Mask 3, Photographs, DeVilbiss Healthcare Inc., DeVilbiss Seal-Ring and CPAP Mask Kit (medium), Part 73510-669.
Mask 4 Photographs, Respironics Inc., Monarch Mini Mask with Pressure Port. Part # 572004, Monarch Headgear, Part # 572011.
Mask 5 Photographs, Healthdyne Technologies, Nasal CPAP Mask (medium narrow), Part # 702510.
Mask 6 Photographs, Healthdyne Technologies, Soft Series Nasal CPAP Mask, Part # 702020.
Mask 7 Photographs, DeVilbiss Healthcare Inc., Small Mask and Seal Rings, Part # 73510-668.
Mask 8 Photographs, Respironics Inc., Reusable Contour Mask (medium), Part # 302180.
Mask 9 Photographs, Healthdyne Technologies, Healthdyne Large Headgear.
Mask 10 Photographs, Respironics Inc., Soft Cap (medium), Part # 302142.
Mask 11 Photographs, Weinmann: Hamburg, Nasalmaskensystem mit Schalldämpfer (medium), Part # WN 23105.
Mask 12 Photographs, Life Care.
Mask 13 Photographs, Healthdyne Technologies.
Mask 14 Photograph, King System.
Mask 15 Photographs, Respironics Inc., Paediatric Mask.
Mask 16 Photographs, Hans Rudolph Inc., Hans Rudolph Silicone Rubber Face Mask/8900.
Partial European Search Report issued in related European Application No. 10 18 3335 (Dec. 28, 2010).
European Search Report issued in related European Application No. 10 18 2727.7 (Dec. 10, 2010).
Japanese Office Action dated Feb. 17, 2009 (3 pgs) and English translation (3 pgs).
English translation of Japanese Office Action issued in Japanese Appln. No. 533420/1998 (Jan. 6, 2004), 3 pgs.
European Office Action issued in Appln. No. 98901876.7 (Feb. 16, 2004), 2 pgs.
PCT International Search Report, PCT/AU2004/000207 (Apr. 28, 2004).
PCT International Search Report, PCT/AU2005/000515 (Jun. 2, 2005).
PCT International Preliminary Report on Patentability, PCT/AU2005/000515 (Oct. 11, 2006), 8 pgs.
U.S. Appl. No. 10/298,845, Kwok, filed Nov. 19, 2002.
European Search Report issued in related European Application No. 10183335.8 (Apr. 13, 2011).
Instruction Brochure for "E-vent-N" Aug. 1997, © Dräger Medizintechnik GmbH, 2 pages.
Translation of Official Action for Japanese Patent Application No. 2001-381410 issued Jun. 6, 2007 (2 pages).

* cited by examiner

RESPIRATORY MASK ASSEMBLY WITH VENT

CROSS REFERENCE TO RELATED APPLICATIONS

This application is a continuation of U.S. application Ser. No. 10/364,358, filed Feb. 12, 2003, now U.S. Pat. No. 7,207,335, which is a continuation of U.S. application Ser. No. 09/021,541, filed Feb. 10, 1998, now U.S. Pat. No. 6,561,190, which claims the benefit of Australian Application No. PO5045, filed Feb. 10, 1997, each incorporated herein by reference in its entirety.

FIELD OF THE INVENTION

The present invention relates to a mask and a vent assembly therefor.

The mask and vent assembly according to the invention have been developed primarily for the venting of washout gas in the application of continuous positive airway pressure (CPAP) treatment in conjunction with a system for supplying breathable gas pressurised above atmospheric pressure to a human or animal. Such a system is used, for example, in the treatment of obstructive sleep apnea (OSA) and similar sleep disordered breathing conditions. However, the invention is also suitable for other purposes including, for example, the application of assisted ventilation or respiration.

The term "mask" is herein intended to include face a, nose masks, mouth masks, nasal pillows, appendages in the vicinity of any of these devices and the like.

BACKGROUND OF THE INVENTION

Treatment of OSA by CPAP flow generator systems involves the continuous delivery of air (or other breathable gas) pressurised above atmospheric pressure to a patient's airways via a conduit and a mask.

For either the treatment of OSA or the application of assisted ventilation, the pressure of the gas delivered to a patient can be at a constant level, bi-level (ie. in synchronism with patient inspiration and expiration) or autosetting in level to match therapeutic need. Throughout this specification the reference to CPAP is intended to incorporate a reference to any one of, or combinations of, these forms of pressure delivery.

The masks used in CPAP treatment generally include a vent for washout of the gas to atmosphere. The vent is normally located in the mask or in the gas delivery conduit adjacent the mask. The washout of gas through the vent is essential for removal of exhaled gases from the breathing circuit to prevent carbon dioxide "re-breathing" or build-up, both of which represent a health risk to the mask wearer. Adequate gas washout is achieved by selecting a vent size and configuration that will allow a minimum safe gas flow at the lowest operating CPAP pressure, which, typically can be as low as around 4 cm $H_2O$ for adults and 2 cm $H_2O$ in paediatric applications.

Prior art masks are generally comprised of a rigid plastic shell which covers the wearer's nose and/or mouth. A flexible or resilient rim (or cushion) is attached to the periphery of the shell which abuts and seals against the wearer's face to provide a gas-tight seal around the nose and/or mouth.

A prior art washout vent utilized one or more holes or slits in the rigid shell or in a rigid portion of the delivery conduit to allow the washout gas to vent to atmosphere. In some masks, the holes or slits were formed during the moulding process. In others, they were drilled or cut as a separate step after the shell or conduit had been moulded.

The flow of gas out the holes or slits in the shell or conduit to atmosphere creates noise and turbulence at the hole or slit outlet as the delivered gas, and upon expiration, the patient-expired gas (including $CO_2$) exits. Bi-level and autosetting gas delivery regimes tend to generate more noise than a constant level gas delivery regime. This is thought to be due to the extra turbulence created by the gas accelerating and decelerating as it cycles between relatively low and relatively high pressures. The noise adversely affects patient and bed-partner comfort.

Another prior art vent included hollow rivets or plugs manufactured from stainless steel or other rigid materials attached to openings in the rigid shell. The outer edges of die rivers were rounded to help reduce noise. However, his approach was expensive, required an extra production step and did not prove effective in reducing noise.

Another approach to reduce noise involved the use of sintered filters at the gas outlet of the mask shell. However, the filters were prone to blocking, especially in the presence of moisture. Accordingly, sintered filters were impractical for use in CPAP treatment as they were easily blocked by the moisture from the patient's respiratory system or humidifiers or during the necessary regular cleaning of the mask and associated componentry.

Foam filters wrapped around the air outlets in the shell were also attempted. However, they also suffered from the disadvantages of being prone to blocking, difficult to clean and requiring constant replacement.

Remote outlet tubes have been used to distance the noise source from the patient. However, these tubes are difficult to clean, are prone to entanglement by the patient and/or their bed partner and suffer the ether disadvantage that a volume of exhausted gas is retained in the tube adjacent the mask.

It is all object of the present invention to substantially overcome or at least ameliorate the prior art disadvantages and, in particular, to reduce the noise generated by gas washout through a mask.

SUMMARY OF THE INVENTION

Accordingly, the invention, in a first aspect, discloses a mask for use with a system for supplying breathable gas pressurised above atmospheric pressure to a human or animal's airways, the mask includes a mask shell which is, in use, in fluid communication with a gas supply conduit, a gas washout vent assembly, wherein at least the region of the mask shell or conduit surrounding or adjacent the vent assembly is formed from a relatively flexible elastomeric material.

In an embodiment, the entire mask is formed from the elastomeric material.

In another embodiment, the mask shell and/or conduit is formed from a relatively rigid material and the region surrounding or adjacent the vent assembly is formed from the relatively flexible elastomeric material.

In a second aspect, the invention discloses a vent assembly for the washout of gas from a mask or conduit used with a system for supplying breathable gas pressure above atmospheric pressure to a human or animal, wherein the vent assembly is formed from the relatively flexible elastomeric material.

In a preferred embodiment, the vent assembly is an insert of relatively flexible elastomeric material, wherein the insert is attachable to the mask shell or conduit. The insert preferably has at least one orifice therethrough.

In a preferred form, the rigid plastics mask shell is formed from polycarbonate and the insert is formed from SILASTIC™ or SANTOPRENE™.

Desirably, the insert is substantially crescent-shaped and includes a plurality of orifices therethrough.

The insert preferably includes a groove around its periphery, the groove adapted to locate the insert against a correspondingly sized rim of an opening formed in the mask shell or conduit.

In other embodiments, the insert is substantially circular, triangular, cross or peanut shaped.

The mask shell and/or the conduit can desirably also include one or more inserts.

BRIEF DESCRIPTION OF THE DRAWINGS

Preferred embodiments of the invention will now be described, by way of examples only, with reference to the accompanying drawings in which.

DESCRIPTION OF THE PREFERRED EMBODIMENTS

Figure 1:
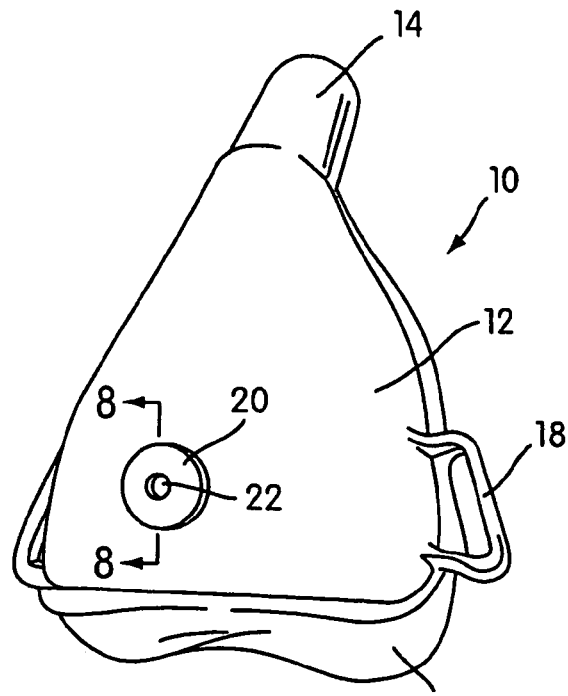
FIG. 1 is a perspective view of a first embodiment.
Figure 2:
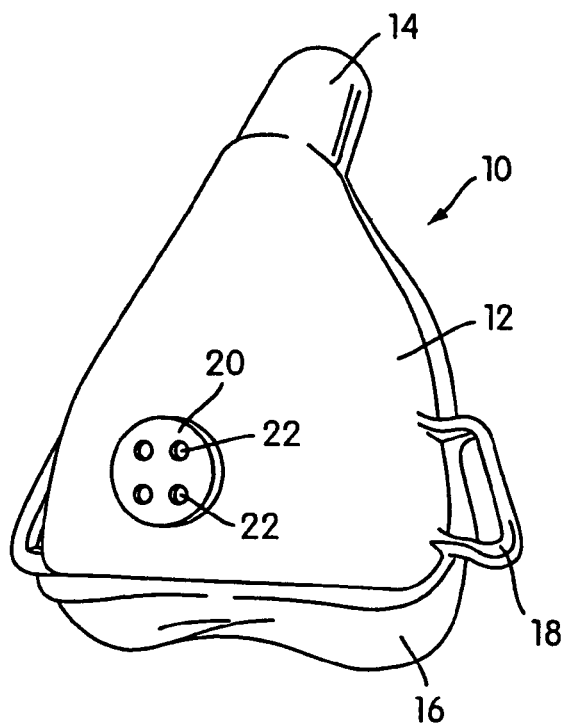
FIG. 2 is a perspective view of a second embodiment.

Referring firstly to FIG. 1, there is shown a mask 10 for use with a system (not shown) for supplying breathable gas pressurised above atmospheric pressure to a human or animal's airways. The mask includes a rigid plastics shell 12 having an inlet tube 14 for connection to a supply conduit to communicate breathable gas from a flow generator (not shown) to the nasal passages of the mask wearer. The mask shell 12 also includes a flexible sealing membrane 16 which is used to provide a gas tight seal between the face of the wearer and the interior of the shell 12. The shell 12 also includes lugs 18 for connecting the mask 10 to a head strap (not shown) to retain the mask in place.

Figure 8:
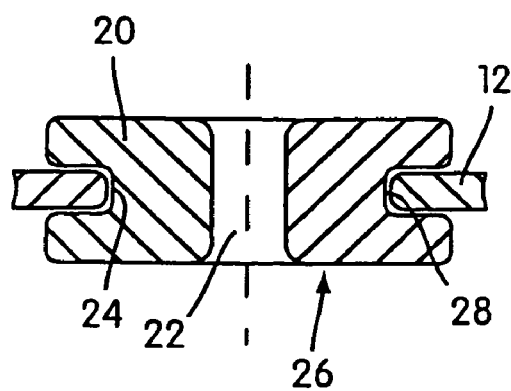
FIG. 8 is a partial cross-sectional view of the first embodiment along the line 8-8 of FIG. 1.

The mask includes a SILASTIC™ insert 20 through which is provided an orifice 22 for gas washout. As best shown in FIG. 8, the insert 20 has a recess or groove 24 around its periphery. A correspondingly sized opening 26 bounded by a rim 28 is provided in the shell 12 to enable the insert 20 to be retained in place in the fashion of a grommet. The opening 26 can be moulded in the shell 12 or drilled or punched as a post-moulding step. The flexibility of the SILASTIC™ allows the insert 20 to be initially squeezed through the opening 26 before resiliently expanding to the configuration shown in FIG. 8 and engaging the rim 28.

As seen in FIG. 8, orifice 22 has a cross-sectional contour from a face side of the orifice to an atmosphere side of the orifice. In FIG. 8, the contour is shown as being symmetrical between the face side of the orifice and the atmosphere side of the orifice with a central portion of the orifice contour being of constant diameter. After the insert 20 is positioned in opening 26 of mask shell 12, the contour remains substantially constant in size as gas is passed therethrough.

FIGS. 2 to 7 show further embodiments in which corresponding reference numerals are used to indicate like features. In all these embodiments the insert 20 has an external groove or recess 24 which engages the rim 28 of a correspondingly shaped opening 26 in the mask shell 12 to retain the insert 20 in place.

In the embodiment shown in FIGS. 2 to 5 and 7 the insert 20 includes more than one orifice 22. In the embodiment shown in FIG. 6, two inserts 20 are provided in the shell 12.

Figure 9:
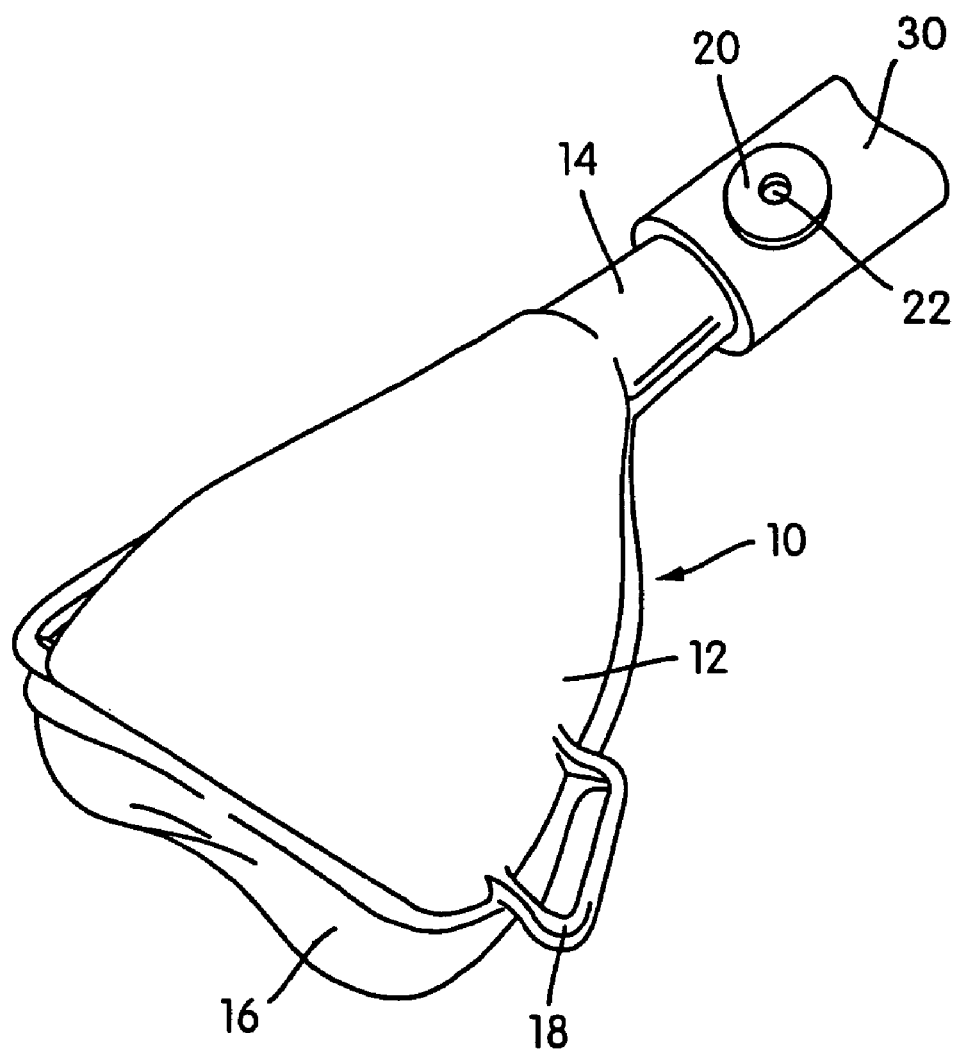
FIG. 9 is a perspective view of an eighth embodiment.

In the embodiment shown in FIG. 9, the insert 20 is provided in a gas supply conduit 30.

Figure 3:
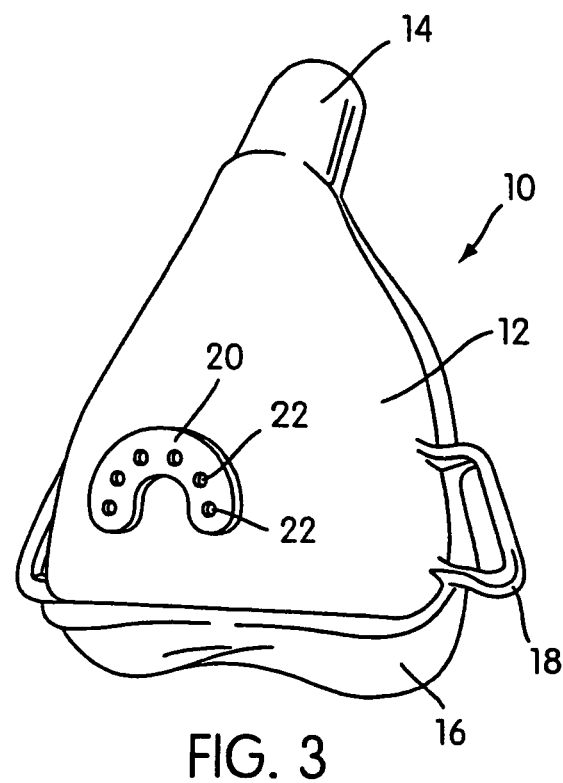
FIG. 3 is a perspective view of a third embodiment.
Figure 4:
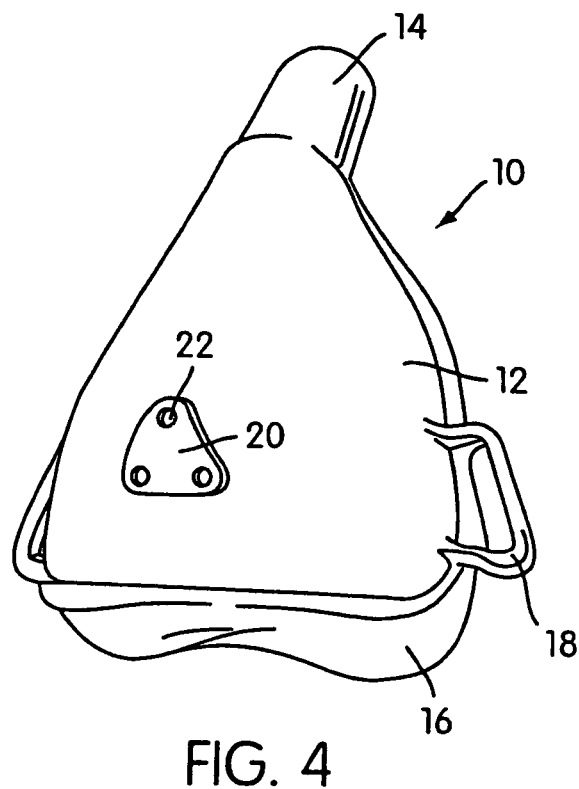
FIG. 4 is a perspective view of a fourth embodiment.
Figure 5:
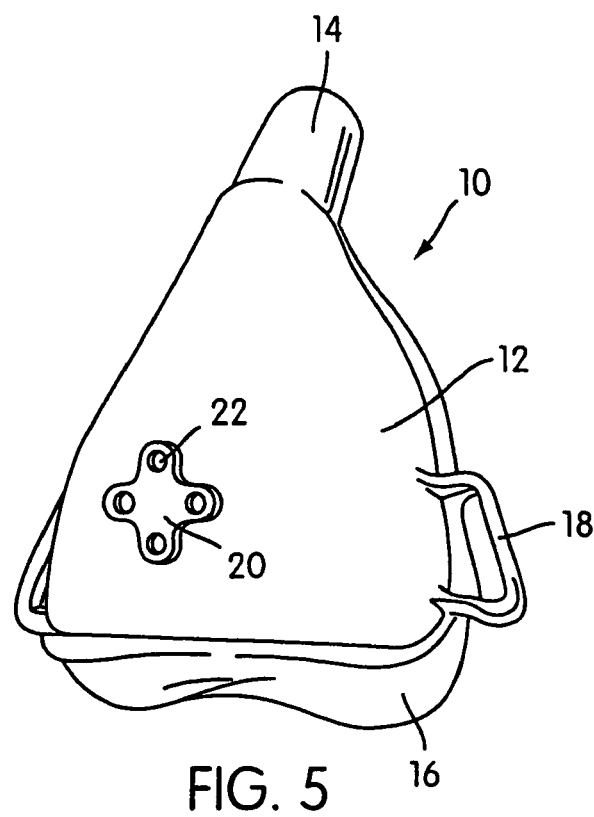
FIG. 5 is a perspective view of a fifth embodiment.
Figure 6:
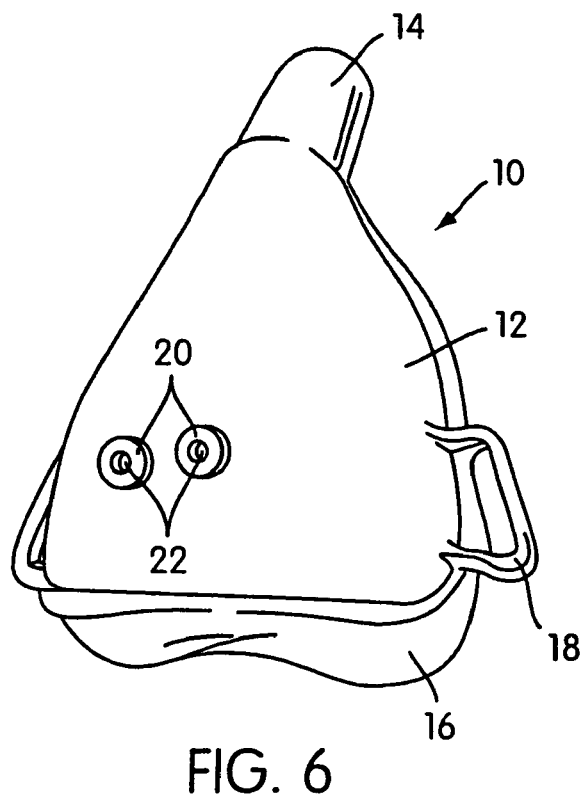
FIG. 6 is a perspective view of a sixth embodiment.
Figure 7:
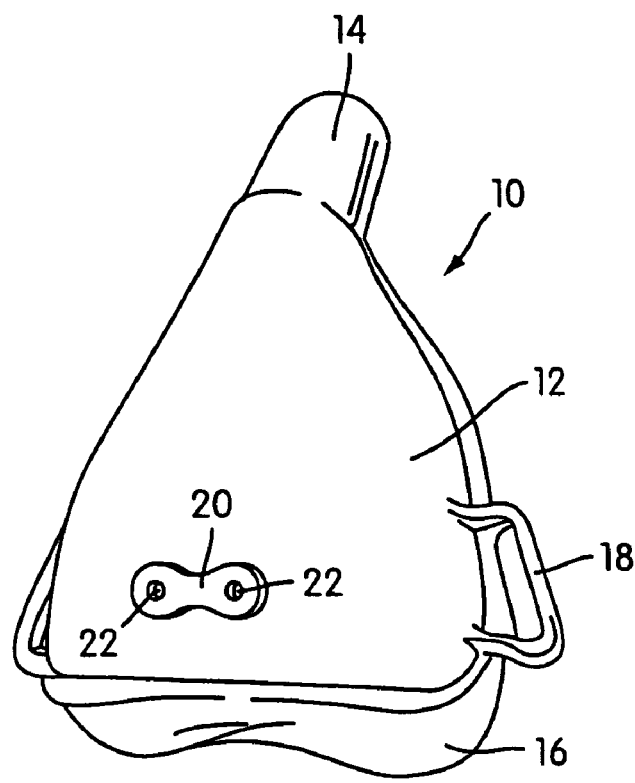
FIG. 7 is a perspective view of a seventh embodiment.
Figure 10:
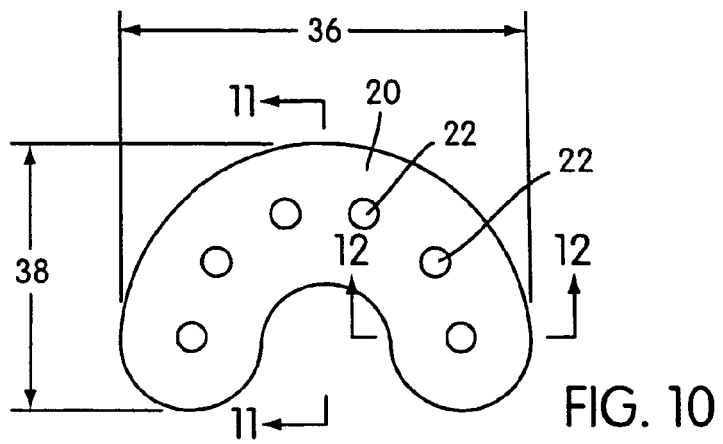
FIG. 10 is a plan view of the insert of the third embodiment.
Figure 11:
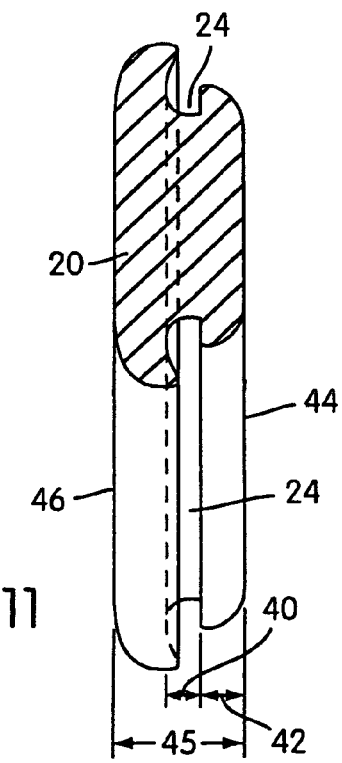
FIG. 11 is a cross-sectional view of the third embodiment insert along the line 11-11 of FIG. 10.
Figure 12:
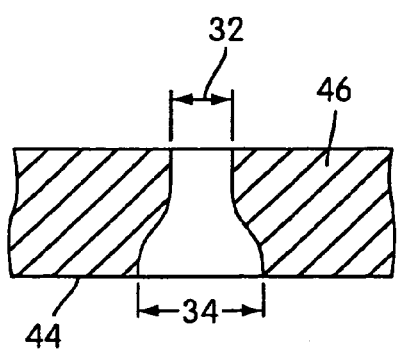
FIG. 12 is a partial cross-sectional view of the third embodiment insert along the line 12-12 of FIG. 10.

FIGS. 10 to 12 show the insert 20 of the third embodiment of FIG. 3. The dimensions 32, 34, 36, 38, 40, 42 and 45 are approximately diameter 1.73 mm, diameter 3.30 mm, 28.80 mm, 19.00 mm, 1.20 mm, 1.20 mm and 3.60 mm respectively.

The side 44 of the insert 20 faces the patient's face in use and the side 46 faces atmosphere.

The mask shell 12 is manufactured from polycarbonate. Other rigid plastics materials can equally be used. The insert 20 can be manufactured from an elastomer sold as SILASTIC™ produced by the Dow Corning Corporation) or a thermoplastic elastomer sold as SANTOPRENE™ (produced by Monsanto). Other flexible elastomeric materials can be used also.

The mask 10 produces less noise than an identical mask having a similar sized and shaped orifice(s) formed directly in the mask shell 12 instead of formed in the flexible insert 20. It is thought that the noise reduction occurs due to the flexible insert 20 damping vibrations caused by air passage through the orifice(s) 22 which produce vibrations or similar in the mask shell 12.

A prototype of the embodiment of the invention shown in FIG. 3 has been tested over a range of constant and bi-level CPAP treatment pressures. For comparison purposes, an identical mask to that shown in FIG. 3 but formed entirely from polycarbonate and having six identical arcuately spaced holes 22 drilled directly through the mask shell was also tested. In both masks the six holes had a diameter of 1.7 mm. The results of the test are summarised in the Tables below:

TABLE 1

Constant level gas delivery

| Pressure | Noise levels 1 m from mask (dBA) | |
|---|---|---|
| (cm H$_2$O) | With flexible insert | Without flexible insert |
| 4 | 26.8 | 35.2 |
| 10 | 33.4 | 43.1 |
| 18 | 39.3 | 49.2 |

TABLE 2

Bi-level gas delivery

| Pressure | Noise levels 1 m from mask (dBA) | |
|---|---|---|
| (cm H$_2$O) | With flexible insert | Without flexible insert |
| 5-10 | 30.8-38.5 | 37.2-43.0 |
| 10-15 | 38.6-43.7 | 42.9-47.9 |

As the result show, the mask shown in FIG. 3 produced less radiated noise than a similar mask not including the flexible elastomeric insert 20 representing a significant advantage in terms of the comfort of the mask wearer and their bed partner.

In addition to the noise reduction discussed above, the masks 10 possesses other advantages over those of the prior art. Firstly, the insert 20 is very easy to install into the mask shell 12 during either assembly of the mask which, is often supplied in kit form, or before and after cleaning which is regularly required and often carried out in the home environment. Secondly, the mask shell 12 may be produced with a single size of opening 26 and provided with a range of different inserts 20 which allows the outlet size to be "tuned" to give an optimum gas washout rate for a particular patient's treatment pressure level.

Although the invention has been described with reference to specific examples, it will be appreciated by those skilled in the art, that the invention may be embodied in many other forms.

We claim:

1. A CPAP mask assembly for use with a system for supplying breathable gas pressurized above atmospheric pressure to a user for treatment of obstructive sleep apnea, the CPAP mask assembly comprising:
   a mask having an inlet tube that is, in use, adapted to be in fluid communication with a gas supply conduit, said mask including a shell made from polycarbonate or another rigid plastic material, the shell being provided with a sealing membrane to provide a gas tight seal with the user in use; and
   a vent including a plurality of gas washout orifices regularly separated and spaced from one another, each said orifice having an inner side that, in use, is positioned towards the user's face, and an outer side that, in use, is positioned adjacent atmosphere, each said orifice being open in use at least during the inhalation and exhalation phases of the user's breathing cycle, wherein
   the vent includes an insert and the orifices are provided in the insert,
   wherein the use of the insert in the mask reduces the decibel noise levels 1 meter from the mask.

2. A CPAP mask assembly as claimed in claim 1, wherein a cross-sectional size or area of each orifice at the inner side is larger than a cross-sectional size or area of the orifice at the outer side, and a transition portion between the inner and outer sides of each said orifice has a cross-sectional size or area that varies or tapers along at least a portion of a length thereof.

3. A CPAP mask assembly as claimed in claim 2, wherein the inner side of each orifice is larger than the outer side.

4. A CPAP mask assembly as claimed in claim 1, wherein the vent includes at least three orifices.

5. A CPAP mask assembly as claimed in claim 1, wherein the vent includes at least four orifices.

6. A CPAP mask assembly as claimed in claim 1, wherein the vent includes at least five orifices.

7. A CPAP mask assembly as claimed in claim 1, wherein the vent includes six orifices.

8. A CPAP mask assembly as claimed in claim 1, wherein a ratio of an inner diameter at the inner side of the orifice to an outer diameter at the outer side of the orifice is about 1.9.

9. A CPAP mask assembly as claimed in claim 1, wherein the length of each said orifice is greater than an inner diameter at the inner side of each said orifice.

10. A CPAP mask assembly as claimed in claim 1, wherein said orifices are separated from each other by at least a diameter of the orifice at the outer side.

11. A CPAP mask assembly as claimed in claim 1, wherein an axis defined within each orifice extends substantially linearly from the inner side to the outer side.

12. A CPAP mask assembly as claimed in claim 1, further comprising a headgear strap and a lug on each side of the shell for connecting the mask to the headgear strap to retain the mask in place relative to the user in use.

13. A CPAP mask assembly as claimed in claim 12, wherein the vent is provided generally between the lugs.

14. A CPAP mask assembly as claimed in claim 1, wherein the length of each orifice is about 3 times a thickness of the shell.

15. A CPAP mask assembly as claimed in claim 1, wherein the length of each said orifice is about 3.60 mm, and each said orifice has an inner diameter at the inner side of about 3.30 mm, and an outer diameter at the outer side of about 1.73 mm.

16. A CPAP mask assembly as claimed in claim 1, wherein the insert is constructed of an elastomeric material.

17. A CPAP mask assembly as claimed in claim 1, wherein the orifices form a pattern generally in the shape of a square or diamond.

18. A CPAP mask assembly as claimed in claim 1, further comprising the gas supply conduit, wherein the orifices are provided to the gas supply conduit.

19. A CPAP mask assembly as claimed in claim 1, wherein each said orifice is substantially cylindrical in shape.

20. A CPAP mask assembly as claimed in claim 1, wherein the orifices are provided to the shell.

21. A CPAP mask assembly as claimed in claim 20, wherein each said orifice extends from the inner side to the outer side of the shell.

22. A CPAP mask assembly as claimed in claim 1, wherein the orifices are substantially linearly aligned.

23. A CPAP mask assembly as claimed in claim 1, wherein the orifices are regularly spaced along an arc.

24. A CPAP mask assembly as claimed in claim 1, wherein the vent is in general vertical alignment with the inlet tube, the vent including six orifices.

25. A CPAP mask assembly as claimed in claim 1, wherein the insert includes a main body providing said orifices, and at least one portion of the insert includes an inner flange portion defining a first surface that engages an inner surface of the mask and an outer flange portion defining a second surface that engages an outer surface of the mask, and the main body, inner flange portion, and outer flange portion comprise one piece of a common material.

26. A CPAP mask assembly as claimed in claim 1, further comprising a rim and groove arrangement to attach the insert to the mask.

27. A CPAP mask assembly as claimed in claim 26, wherein the mask includes a rim adapted to engage a groove of the insert.

28. A CPAP mask assembly for use with a system for supplying breathable gas pressurized above atmospheric pressure to a user for treatment of obstructive sleep apnea, the CPAP mask assembly comprising:
   a mask adapted to be in fluid communication with a gas supply conduit; and
   a flexible elastic vent portion provided to the mask, the vent portion including at least four gas washout orifices regularly separated and spaced from one another,
   each said orifice having an inner side and an outer side,
   wherein a cross-sectional size or area of each orifice at the inner side is larger than a cross-sectional size or area of the orifice at the outer side,
   wherein the use of the vent portion in the mask reduces the decibel noise levels 1 meter from the mask.

29. A CPAP mask assembly as claimed in claim 28, wherein the inner side, in use, is positioned towards the user's face, and the outer side, in use, is positioned adjacent atmosphere, each said orifice being open in use at least during the inhalation and exhalation phases of the user's breathing cycle.

30. A CPAP mask assembly as claimed in claim 29, wherein the inner side of the vent portion extends inside the mask and the outer side of the vent portion extends outside the mask.

31. A CPAP mask assembly as claimed in claim 28, wherein each orifice includes a transition portion between the inner and outer sides that has a cross-sectional size or area that varies or tapers along at least a portion of a length thereof.

32. A CPAP mask assembly as claimed in claim 28, wherein each said orifice has a substantially round cross section along its length.

33. A CPAP mask assembly as claimed in claim 28, wherein the mask includes a mask shell and at least a region of the mask shell surrounding the vent portion is formed from a flexible elastomeric material.

34. A CPAP mask assembly as claimed in claim 33, wherein the entire mask shell is formed from the relatively flexible elastomeric material.

35. A CPAP mask assembly as claimed in claim 33, wherein the relatively flexible elastomeric material includes one of SILASTIC™ and SANTOPRENE™.

36. A CPAP mask assembly as claimed in claim 28, wherein a ratio of an inner diameter at the inner side of the orifice to an outer diameter at the outer side of the orifice is about 1.9.

37. A CPAP mask assembly as claimed in claim 28, wherein the length of each said orifice is greater than an inner diameter at the inner side of each said orifice.

38. A CPAP mask assembly as claimed in claim 28, wherein said orifices are separated from each other by at least a diameter of the orifice at the outer side.

39. A CPAP mask assembly as claimed in claim 28, wherein an axis defined within each orifice extends substantially linearly from the inner side to the outer side.

40. A CPAP mask assembly as claimed in claim 28, wherein the length of each said orifice is about 3.60 mm, and each said orifice has an inner diameter at the inner side of about 3.30 mm, and an outer diameter at the outer side of about 1.73 mm.

41. A CPAP mask assembly as claimed in claim 28, wherein the mask includes a mask shell and a sealing membrane provided to the mask shell.

42. A CPAP mask assembly as claimed in claim 41, wherein the vent portion is raised compared to an inner and outer surface of the mask shell.

43. A CPAP mask assembly as claimed in claim 28, wherein the arc is "U" or "C" shaped.

44. A CPAP mask assembly as claimed in claim 43, wherein the arc is oriented as an upside-down "U" relative to the patient in use.

45. A CPAP mask assembly as claimed in claim 44, wherein the arc is symmetrical about an axis, and three of the orifices are provided on one side of the axis and the other three of the orifices are provided on the other side of the axis.

46. A CPAP mask assembly as claimed in claim 45, wherein one of the orifices is provided at each end portion of the arc.

47. A CPAP mask assembly as claimed in claim 28, wherein the arc is U-shaped and includes two end portions and a central portion connecting the two end portions, and two of the orifices are provided at respective end portions of the arc and the other four of the orifices are regularly spaced and separated from one another along the central portion of the arc.

48. A CPAP mask assembly as claimed in claim 28, wherein the mask includes an inlet tube for connection to the gas supply conduit.

49. A CPAP mask assembly as claimed in claim 48, wherein the vent portion is in general vertical alignment with the inlet tube.

50. A CPAP mask assembly as claimed in claim 28, wherein pressurized gas is provided at a level suitable for CPAP treatment.

51. A CPAP mask assembly as claimed in claim 50, wherein pressurized gas is provided in the range of 4-18 $cmH_2O$.

52. A CPAP mask assembly as claimed in claim 28, wherein said orifices are separated from each other by at least 1.73 mm.

53. A CPAP mask assembly as claimed in claim 28, wherein the length of each said orifice is about 3.60 mm.

54. A CPAP mask assembly as claimed in claim 28, wherein the arc is U-shaped and a height of the arc is less than 19 mm.

55. A CPAP mask assembly as claimed in claim 28, wherein the arc is U-shaped and a width of the arc is less than 28.8 mm.

56. A CPAP mask assembly as claimed in claim 28, wherein each orifice has a volume less than about 30.8 $mm^3$.

57. A CPAP mask assembly as claimed in claim 28, wherein each orifice has a volume of at least 8.5 $mm^3$.

58. A CPAP mask assembly as claimed in claim 28, wherein a difference between an inner diameter at the inner side of the orifice to an outer diameter at the outer side of the orifice is about 1.6 mm.

59. A CPAP mask assembly as claimed in claim 28, wherein the pressurized gas is in the range of 4-18 $cmH_2O$.

60. A mask assembly for continuous positive airway pressure treatment of obstructive sleep apnea, comprising:
    a flexible sealing membrane defining at least a portion of a breathing cavity and structured to provide a gas tight seal between the face of the wearer and the breathing cavity; and
    a vent for washout of exhaled carbon dioxide gas from the breathing cavity, the vent comprising a plurality of orifices, each orifice defining a passage from the breathing cavity to atmosphere wherein the passage has a cross-sectional profile that includes a generally frusto-conical portion and a generally cylindrical portion adjacent the generally frusto-conical portion,
    wherein the use of the vent in the mask assembly reduces the decibel noise levels 1 meter from the mask assembly.

61. A mask assembly as claimed in claim 60, wherein the generally frusto-conical portion has a length and with a larger-diameter end of the frusto-conical portion aligned towards the breathing cavity and a smaller-diameter end of the frusto-conical portion aligned towards atmosphere and the cylindrical portion.

62. A mask assembly as claimed in claim 61, wherein the generally cylindrical portion has a cylinder diameter approximately the same size as the smaller-diameter end of the frusto-conical portion.

63. The mask assembly as claimed in claim 62, further comprising a second generally cylindrical portion having a cylinder diameter approximately the same size as the larger-diameter end of the frusto-conical portion.

64. The mask assembly as claimed in claim 62, wherein the sum of the lengths of the generally frusto-conical portion and the generally cylindrical portion is greater than a surrounding thickness of the mask assembly.

65. The mask assembly as claimed in claim 62, wherein the cylinder diameter is approximately half the larger-diameter end of the frusto-conical portion.

66. The mask assembly as claimed in claim 62, wherein the diameter of an orifice adjacent atmosphere is approximately 1.73 mm.

67. The mask assembly as claimed in claim 62, wherein the diameter of an orifice adjacent the breathing cavity is approximately 3.3 mm.

68. The mask assembly as claimed in claim 60, wherein a thickness of the cross-sectional profile is approximately 3.6 mm.

69. The mask assembly as claimed in claim 60, wherein the vent comprises molded silicone.

70. The mask assembly as claimed in claim 60, wherein the vent is formed from a flexible elastomeric material.

71. The mask assembly as claimed in claim 60, wherein an end of the generally cylindrical portion is adjacent atmosphere.

72. The mask assembly as claimed in claim 60, wherein the orifices of the vent are arranged on an arc.

73. The mask assembly as claimed in claim 60, wherein the vent includes six orifices.

74. The mask assembly as claimed in claim 60, wherein the flexible sealing membrane includes nasal pillows.

75. The mask assembly as claimed in claim 60, wherein the vent is provided on one side of the mask assembly and the flexible sealing membrane is provided on the opposite side of the mask assembly.

76. The mask assembly as claimed in claim 60, further comprising a shell to support the flexible sealing membrane and define at least a portion of the breathing cavity, the vent being provided to the shell.

77. The mask assembly as claimed in claim 76, wherein the shell is formed from a flexible elastomeric material.

78. The mask assembly as claimed in claim 76, wherein the shell is formed from a relatively rigid material.

79. The mask assembly as claimed in claim 60, wherein the vent includes six orifices arranged on an arc.

80. A mask assembly as claimed in claim 79, wherein the arc is "U" or "C" shaped.

81. A mask assembly as claimed in claim 80, wherein the arc is oriented as an upside-down "U" relative to the patient in use.

82. A mask assembly as claimed in claim 81, wherein the arc is symmetrical about an axis, and three of the orifices are provided on one side of the axis and the other three of the orifices are provided on the other side of the axis.

83. A CPAP mask assembly for use with a system for supplying breathable gas pressurized above atmospheric pressure to a user for treatment of obstructive sleep apnea, the CPAP mask assembly comprising:
a mask having an inlet tube that is, in use, adapted to be in fluid communication with a gas supply conduit, said mask including a shell and a seal provided to the shell to provide a gas tight seal with the user in use; and
a vent provided to the mask, the vent including at least four gas washout orifices arranged in two or more columns, each orifice being open in use and having a cross-sectional area at a first side that is larger than a cross-sectional area at a second side opposite the first side,
wherein the use of the vent in the mask reduces the decibel noise levels 1 meter from the mask.

84. A CPAP mask assembly as claimed in claim 83, wherein the seal includes nasal pillows.

85. A CPAP mask assembly as claimed in claim 83, wherein each orifice includes a transition portion between the first and second sides that has a cross-sectional area that vanes or tapers along at least a portion of a length thereof.

86. A CPAP mask assembly as claimed in claim 83, wherein the shell includes a lug on each side thereof for connecting the mask to a headgear strap to retain the mask in place relative to the user in use.

87. A CPAP mask assembly as claimed in claim 83, wherein the orifices form a pattern generally in the shape of a square.

88. A CPAP mask assembly as claimed in claim 83, wherein each said orifice has a substantially round cross section along its length.

89. A CPAP mask assembly as claimed in claim 83, wherein the vent includes an insert and the orifices are provided in the insert.

90. A CPAP mask assembly as claimed in claim 89, further comprising a rim and groove arrangement to attach the insert to the mask.

91. A CPAP mask assembly as claimed in claim 90, wherein the mask includes a rim adapted to engage a groove of the insert.

92. A CPAP mask assembly as claimed in claim 89, wherein the insert includes a main body providing said orifices, and at least one portion of the insert includes an inner flange portion defining a first surface that engages an inner surface of the mask and an outer flange portion defining a second surface that engages an outer surface of the mask, and the main body, inner flange portion, and outer flange portion comprise only a single piece of a common material.

93. A CPAP mask assembly for use with a system for supplying breathable gas pressurized above atmospheric pressure to a user for treatment of obstructive sleep apnea, the CPAP mask assembly comprising:
a mask having an inlet tube that is, in use, adapted to be in fluid communication with a gas supply conduit, said mask including a shell made from polycarbonate or another rigid plastic material, the shell being provided with a sealing membrane to provide a gas tight seal with the user in use;
a vent including at least four gas washout orifices regularly separated and spaced from one another, each said orifice having an inner side that, in use, is positioned towards the user's face, and an outer side that, in use, is positioned adjacent atmosphere, wherein a cross-sectional size or area of each orifice at the inner side is larger than a cross-sectional size or area of the orifice at the outer side, and a transition portion between the inner and outer sides of each said orifice has a cross-sectional size or area that varies or tapers along at least a portion of a length thereof; and
a headgear strap and a lug on each side of the shell for connecting the mask to the headgear strap to retain the mask in place relative to the user in use,
wherein the vent is provided generally between the lugs and in general vertical alignment with the inlet tube,
wherein the use of the vent in the mask reduces the decibel noise levels 1 meter from the mask.

94. A CPAP mask assembly as claimed in claim 93, wherein the vent includes an insert and the orifices are provided in the insert.

95. A CPAP mask assembly as claimed in claim 94, further comprising a rim and groove arrangement to attach the insert to the mask.

96. A CPAP mask assembly as claimed in claim 95, wherein the mask includes a rim adapted to engage a groove of the insert.

97. A CPAP mask assembly as claimed in claim 94, wherein the insert includes a main body providing said orifices, and at least one portion of the insert includes an inner flange portion defining a first surface that engages an inner surface of the mask and an outer flange portion defining a second surface that engages an outer surface of the mask, and the main body, inner flange portion, and outer flange portion comprise one piece of a common material.

98. A CPAP mask assembly as claimed in claim 93, wherein the orifices are provided to the inlet tube.

99. A CPAP mask assembly as claimed in claim 93, wherein the orifices are arranged in two or more columns.

100. A mask assembly for continuous positive airway pressure treatment of obstructive sleep apnea, comprising:
- a flexible sealing membrane defining at least a portion of a breathing cavity and structured to provide a gas tight seal between the face of the wearer and the breathing cavity; and
- a vent for washout of exhaled carbon dioxide gas from the breathing cavity, the vent comprising at least four orifices,
- each orifice defining a passage from the breathing cavity to atmosphere wherein the passage has a cross-sectional profile that includes a generally frusto-conical portion and a generally cylindrical portion adjacent the generally frusto-conical portion,
- wherein the generally frusto-conical portion has a length and with a larger-diameter end of the frusto-conical portion oriented generally towards the breathing cavity and a smaller-diameter end of the frusto-conical portion oriented generally towards atmosphere and the cylindrical portion, and the generally cylindrical portion has a cylinder diameter approximately the same size as the smaller-diameter end of the frusto-conical portion,
- wherein the use of the vent in the mask assembly reduces the decibel noise levels 1 meter from the mask assembly.

101. A CPAP mask assembly for use with a system for supplying breathable gas pressurized above atmospheric pressure to a user for treatment of obstructive sleep apnea, the CPAP mask assembly comprising:
- a mask having an inlet tube that is, in use, adapted to be in fluid communication with a gas supply conduit, said mask including a shell made from polycarbonate or another rigid plastic material, the shell being provided with a flexible sealing membrane to provide a gas tight seal with the user in use;
- strap attachment points provided to the shell to connect the mask to a head strap; and
- a vent provided to the shell, the vent including at least four gas washout orifices,
- wherein each orifice is open in use and has a cross-sectional area at a first side that is larger than a cross-sectional area at a second side opposite the first side,
- wherein the use of the vent in the mask reduces the decibel noise levels 1 meter from the mask.

102. A CPAP mask assembly as claimed in claim 101, wherein each orifice includes a transition portion between the first and second sides that has a cross-sectional size or area that varies or tapers along at least a portion of a length thereof.

103. A CPAP mask assembly as claimed in claim 102, wherein each said orifice has a substantially round cross section along its length.

104. A CPAP mask assembly as claimed in claim 103, wherein the pressurized gas is in the range of 4-18 cmH$_2$O.

105. A CPAP mask assembly as claimed in claim 104, wherein the orifices are regularly spaced along an arc.

106. A CPAP mask assembly as claimed in claim 104, wherein the orifices are arranged in two or more columns, each column including at least two said orifices.

* * * * *